United States Patent [19]

Lyman

[11] 4,073,695

[45] Feb. 14, 1978

[54] LEIGHTON TUBE

[75] Inventor: George F. Lyman, Weston, Mass.

[73] Assignee: Data Packaging Corporation, Cambridge, Mass.

[21] Appl. No.: 713,441

[22] Filed: Aug. 11, 1976

[51] Int. Cl.$^2$ .......................... C12K 1/00; C12K 9/00
[52] U.S. Cl. ..................................... 195/127; 195/139
[58] Field of Search ............................... 195/127, 139

[56] References Cited

U.S. PATENT DOCUMENTS

| 2,947,116 | 8/1960 | Earle et al. | 195/139 |
| 3,563,859 | 2/1971 | Fink | 195/139 |
| 3,616,265 | 10/1971 | Calabese et al. | 195/139 |

OTHER PUBLICATIONS

Parker, Methods of Tissue Culture, 3rd Ed., p. 19, (1961), Harper & Row Publishers.

*Primary Examiner*—Alvin E. Tanenholtz
*Attorney, Agent, or Firm*—Wolf, Greenfield & Sacks

[57] ABSTRACT

A Leighton tube assembly designed for the growth of tissue cultures and their preservation comprising a tube, a cover slip and a means to close said tube. The tube, made from two injection molded pieces welded together, has a chamber toward its closed end and a neck towards its open end. The chamber has a wall with a flat portion which is separated from the open end of the tube by a dam located in the neck. The cover slip is molded of a plastic material which is both transparent and inert with respect to most chemical solvents. The cover slip has a culture segment which lies on said flat portion of the chamber wall when the slip is in its growth position and a handle. The handle is of a length which allows the positioning of a cap over the open end of the tube.

15 Claims, 8 Drawing Figures

U.S. Patent  Feb. 14, 1978  4,073,695
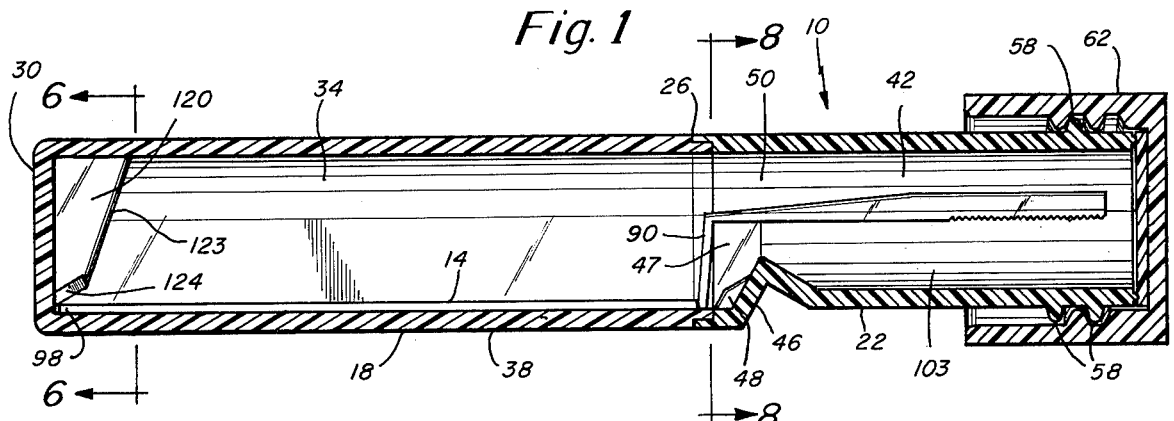
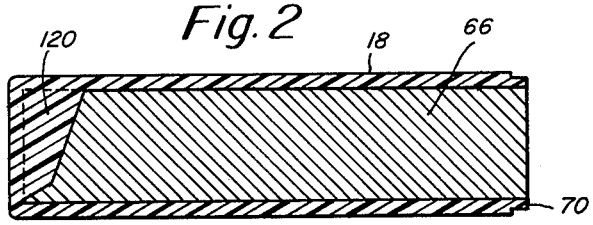
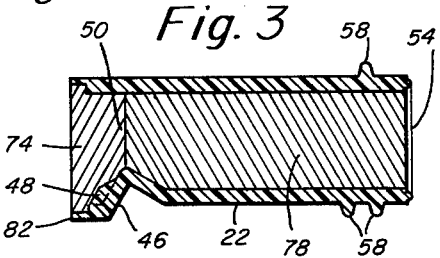
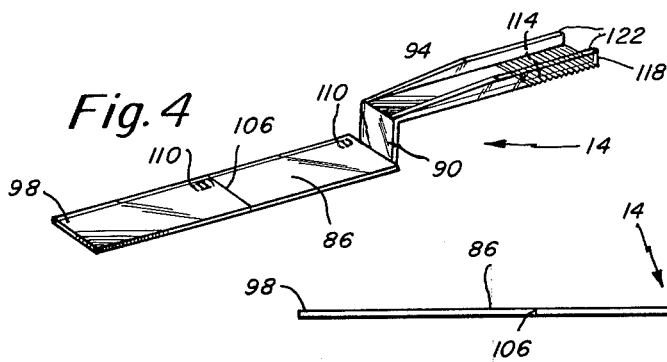
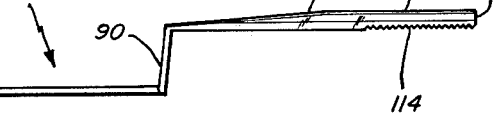
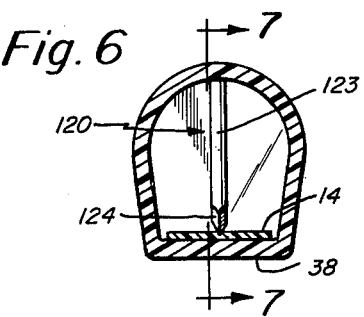
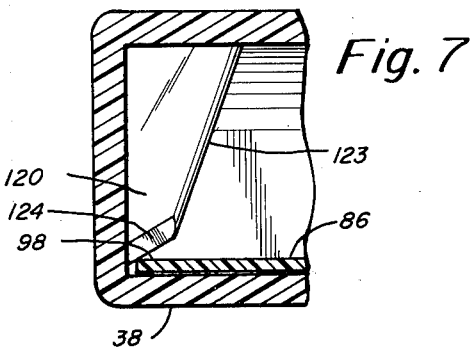
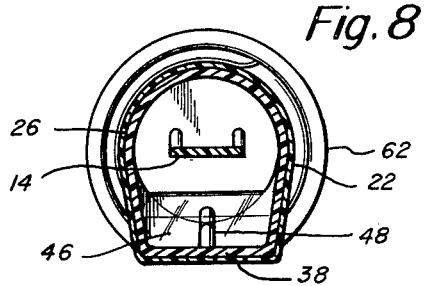

LEIGHTON TUBE

SUMMARY AND BACKGROUND OF THE INVENTION

The typical Leighton tube consists of a glass tube to be used in conjunction with a flat thin glass cover slip. Tissue cultures are grown in such a Leighton tube by placing appropriate media in the tube along with the cells to be cultured. The use of such tubes, with their concomitant cover slip, allows the user to stain cultures. Such staining capability is valuable in a variety of experimental tests situations. Further because of the flat shape of the cover slip and its small size, it can be attached to and preserved along with reports associated with such tests or experiments.

Despite the usefulness of the Leighton tubes heretofore used they have certain drawbacks. First, they are difficult and expensive to manufacture. Second, because the cover slips of the prior are made of glass and therefore are flat in shape, they are difficult to handle and retrieve from the inside of the tube. Furthermore, being made of glass, they are prone to breakage. It is among the purposes of the present invention to eliminate some of the disadvantages associated with glass Leighton tubes.

One object of the present invention is to provide a Leighton tube assembly which can be manufactured easily and cheaply from injection moldable plastics.

Another object of the present invention is to provide a Leighton tube with a dam or baffling means to prevent the flow of liquid media out of the tube.

A further object of the present invention is to provide a Leighton tube assembly having a cover slip with a handle so that manipulation of the cover slip (as with tweezers) is facilitated.

Another object of this invention is to provide a cover slip in which the handle is so arranged that the aforementioned dam does not interfere with the proper positioning of the cover slip in the tube.

Still a further object of the present invention is to provide a Leighton tube assembly have a cover slip with a handle which is displaced from the plane of the culture segment thereof so that the latter may lie upon the wall of the tube while the former clears the dam located in the neck of the tube.

Another object of the present invention is to provide means to prevent the light weight cover slip from floating in liquid media placed within the Leighton tube.

Yet another object of the invention is to provide a Leighton tube having a dam and cover slip so constructed that the liquid media placed within the tube chamber does not escape by capillary action.

A further object of the present invention is to provide a Leighton tube assembly with a cover slip the culture segments of which can be cut by a scissors or a knife so that a plurality or portions thereof, with adhering culture, can be attached to more than one report for preservation therewith.

A further object of the present invention is to provide a Leighton tube assembly with a cover slip made of a transparent material which is inert to most chemical solvents so that said cover slip may be used in connection with most experimental and staining treatments which a user may wish to apply. The transparency facilitates accurate observation of cultures grown on the slip.

Another object of the present invention is to provide a Leighton tube in which the cover slip is treated to be wettable so that cells grown within the tube will adhere to the cover slip, which then makes it possible for a user to stain and otherwise test growths on the cover slip.

Still a further object of the present invention is to provide a Leighton tube in which the culture segment is automatically properly positioned in the tube chamber upon insertion of the cover slip.

The Leighton tube of the present invention comprises a tube and a cover slip. The tube has a neck and a chamber, the chamber being toward the closed end of the tube. The neck has a dam formed in it, which is in a blocking position with respect to a flat portion extending longitudinally from the closed end of the chamber. Being of a complicated shape, this tube cannon be made in one piece by an injection molding process because the molds could not be removed from the chamber region after formation. This problem is overcome by making the tube in two pieces. The neck piece, in which the dam is located, can be formed by injection molding material such as polystyrene around two interior molds that can be extracted from either end of the neck piece after formation. The chamber piece only requires but one internal mold and is molded out of the same polystyrene material. After the two pieces are molded, they are welded together to form the complete tube.

Also molded into the closed end of the tube is a guide rib which is located centrally in the upper portion of the closed end and is adapted to guide the cover slip into proper position as it is inserted and to hold the cover slip in place and to prevent it from floating when liquid media is in the tube. The relative ease with which the parts of the tube may be injection molded, with the dam and the ribs located therein, is indicative of the possible savings associated with the cost of manufacture of these tubes as compared with that of conventional glass Leighton tubes.

The cover slip is also molded from a plastic material. It is desirable that the material out of which this cover slip is made be both transparent and unaffected by most chemical solvents. The requirement of transparency arises out of the need for detailed inspection of the cultures grown on the cover slip. The desirability of the relative chemical inertness is a consequence of the needs of users who wish to do experiments and tests on the material on the cover slip. Because the tests and experiments often involve the use of organic solvents which can eat away many plastic materials, the material should be chemically inert. A material having both the desired qualities and which can be used in the molding of the cover slip is called TPX.

The cover slip though formed in one piece has three distinct parts. The culture segment which is flat, a handle and a connecting segment which joins the culture segement and the handle. The culture segment has dimensions such that it may lie flat upon the flat portion of the wall of the chamber with its distal end located underneath the guide rib formed in the closed end of the tube. The connecting segment rises from the culture segment and connects to the handle which lies substantially in a plane parallel to that in which the culture segment lies and is of a height above the culture segment such that when the cover slip is located in its growth position within the tube, the handle clears the dam located in the neck of the tube. The connecting segment rises at an angle that is steeper than the angle the dam makes with the flat portion of the tube, so that when the cover slip is in position the connecting segment and the dam have a wedged shaped gap between them. This gap prevents the liquid from rising in the space between the connecting segment and the dam by capillary action.

The handle is of length such that it does not protrude from the open end of the tube when the cover slip is in its growth position and therefore it does not prevent the cap from being screwed onto the tube. The handle is serrated and further because the handle is not in contact with the walls of the tube when the slip is in place, the handle may be grasped easily and securely, by tweezers, for easy manipulation. To strengthen the handle, ribs are formed along its sides.

Also molded into the neck of the tube is a spacer rib which is located centrally on the chamber side of the dam. This spacer rib maintains a separation between the dam and the cover slip connecting segment, which prevents the undersirable capillary action. The spacer rib also is angled and located so that it acts cooperatively with the guide rib to guide the cover slip into position and hold it in place.

BRIEF FIGURE DESCRIPTION

FIG. 1 is a cross sectional view of a Leighton tube assembly constructed in accordance with the present invention;

FIG. 2 is a cross sectional view of the chamber piece forming part of the tube of FIG. 1 and the interior mold that forms it;

FIG. 3 is a cross sectional view of the neck piece forming part of the tube of FIG. 1 and the interior molds which form it;

FIG. 4 is a perspective view of the cover slip;

FIG. 5 is a side view of the cover slip;

FIG. 6 is a cross section of the assembly taken along line 6—6 in FIG. 1;

FIG. 7 is a fragmentary cross sectional view showing the closed end of the tube and the distal end of the cover slip; and FIG. 8 is a cross section of the assembly taken along line 8—8 of FIG. 1.

DETAILED DESCRIPTION

The Leighton tube assembly shown in the drawings, which is just one embodiment of the present invention, comprises a tube 10 and a cover slip 14. The tube is formed from two pieces, a first or chamber piece 18 as shown in FIG. 2 and a second or neck piece 22 as shown in FIG. 3. The chamber piece 18 is welded to the neck piece 22 as suggested at 26 in FIG. 1. The chamber piece 18 has a closed end 30 and a flat portion 38 and defines the tube chamber 34. the neck piece 22 when welded to the chamber piece 18 defines the tube neck 42. A dam 46 is formed in the neck as seen in FIGS. 1 and 3, and it is on the same side of the tube as the flat portion 38. As the dam does not completely shut off the chamber 34, there is a passage 50 through which the chamber communicates with the rest of the neck 42 and the open end 54 of the tube. External threads 58 are formed on the neck on which the cap 62 may be screwed.

The chamber piece 18 and the neck piece 22 are most conveniently molded from polystyrene. A first mold 66, shown in FIG. 2, is used to form the interior of the chamber piece 18. The chamber piece is formed with a slight draft so that the mold 66 may be extracted from the dam end 70. The neck piece 22 can be injection molded about molds 74 and 78 that part at the dam 46. The mold 74 may be removed from the chamber end 82 of the neck piece, while mold 78 may be removed from the open end 54. Appropriate drafts may be formed in the neck piece to facilitate removal of the molds.

The cross sectional dimensions of the neck are such that the plane in whcih the outside surface of the flat portion 38 lies is not penetrated by any part of the tube. This allows the tube to be located, in its incubating position as shown in FIG. 1, with the flat portion 38 supported on a horizontal planar surface such as a table.

The cover slip 14 is also injection molded out of a plastic material. Preferably, this material is both transparent and inert to most chemical solvents. A material with these desirable qualities mentioned is called TPX. The cover slip has three parts to it: the culture segment 86, a connecting segment 90, and a handle 94. The culture segment is flat in shape and is of such dimensions that it can lie on the flat wall 38 of the tube when the cover slip 14 is in its growth position as shown in FIG. 1. When the cover slip is in that growth position, the distal end 98 of the culture segment is located beneath, and prevented from vertical displacement by, guide rib 120 formed in the closed end 30 of the tube. The guide rib is particularly desirable because of the lightness of the cover slip, which gives it a tendency to float in the media normally placed in the Leighton tube assembly. Guide rib 120 has a smooth surface 123 angling down from the tube wall opposite the flat portion 38 and toward the closed end 30. Upon insertion of the cover slip into the tube the distal end 98 of the culture segment 84 contacts the guide rib and the culture segment is guided into its proper growth position on flat portion 38. The lower portion of guide rib 120 is formed into a knife edge 124 to reduce the friction between the edge and the distal end 98 of the culture segment so that it slides more easily into position. The knife edge also reduces the area of the culture segment that is disturbed upon insertion and removal of the cover slip.

As can be best seen in FIG. 5, the handle 94 is located in a plane which lies parallel to but spaced above the plane in which the culture segment 86 is located. The height of the handle 94 above the culture segment 86 is such that when the cover slip is in its growth position, the handle passes through the passage 50 into the neck 42 when the culture segment 86 rests flat upon the flat portion 38 of the tube chamber. The connecting segment 90 angles upwardly from the culture segment to the handle. And because the dam 46 rests above the bottom of the neck piece as shown in FIGS. 1 and 3, the handle 94 is spaced from the bottom as suggested at 103, and therefore both the top and bottom surfaces of the handle are accessible.

Connecting segment 90 rises more steeply than dam 46, so that the upper end of segment 90 is spaced a greater distance from dam 46 than the lower end. The gap 47 between connecting segment 90 and dam 46 prevents the liquid medium in the chamber from rising between the connecting segment and the dam 46 by capillary action and escaping from chamber 34. Spacer rib 48 formed on the chamber side of dam 46 maintains a separation between connecting segment 90 and dam 46, which further acts to prevent the undesirable capillary action. The spacer rib 48 angles downward to the flat portion and toward the closed end of the tube so that it urges cover slip 14 forward upon the insertion of the cover slip into chamber 34. the distance between guide rib 120 and spacer rib 48 is related to the length of the culture segment 86 so that the spacer rib and guide rib act cooperatively to automatically position the culture segment properly against wall 38 upon insertion of the cover slip.

The material out of which the cover slip if formed is sufficiently soft so that it may be cut by a knife or scissors. Scoring 106 is located on the culture segment 86 in order to guide the cutting. This scoring is located to accurately divide the culture segment in half. Marking 110 (I and II) provides separate identification for the two parts of the culture segment 86 for the convenience of the user. The handle 94 is serrated as at 114 located at its free end 118, which facilitates the gripping of the handle by a tool such as tweezers. In order to add strength to the handle, flanges 122 are provided along each side of the handle.

It should be noted that when the assembly is in its incubating position the flat portion of piece 18, the end wall 30, and the dam 46 provide a reservoir in which the media with its cell culture material may be held. Cells precipitate down out of the media onto the culture segment of the cover slip. These cells adhere to the culture segment because it has been treated to make it wettable.

In use the cover slip 14 is located in the tube in its growth position, and the tube is supported from below with its flat portion in contact with an underlying planar surface such as a table top. Liquid media, carrying appropriately chosen cell cultures, is located in the tube covering the culture segment of the cover slip and is prevented from flowing from the chamber section by the dam located in the neck. The cell material precipitates downward onto the cover slip which is made wettable so that the cell cultures will adhere thereto. The polystyrene material out of which the tube itself is formed is not treated to be wettable so that the culture cells do not adhere to its walls. Because the material out of which the cover slip is made is of a low density the culture segment may have a tendency to float in the liquid media located in the tube. To prevent such floatation the guide rib 120 is positioned to hold down the distal end of the culture segment. When the cells have adhered to the cover slip, it may be removed from the tube and staining or other tests may be carried out on the cell material located on the culture segment. Further, when the experiment or text is completed, the cover slip may be removed and dried. As the plastic material out of which the cover slip is made is cuttable and not prone to breakage, the user may cut off the culture segment and as well cut that segment into two or more pieces. These flat pieces may then be attached to and preserved with the reports made in connection with the test that have been conducted. This ability to cut the segment into separate pieces is one important advantage which plastic cover slips have over the glass cover slips used in the prior art Leighton tube assemblies.

It should be obvious to the reader that the embodiment described herein is just one of many which may be constructed according to the spirit of this invention. Therefore, the scope of this invention is not to be limited to the single embodiment illustrated and described. Rather, the scope is to be determined by the appended claims and their equivalents.

What is claimed is:

1. A Leighton tube assembly comprising
a tube having an inside and an outside, a closed end and an open end, a neck adjacent said open end, a chamber toward said closed end which merges with said neck, means for closing said tube at said open end, and a cover slip,
said chamber having a wall with a flat portion lying, at its outside, in a plane through which no part of said tube penetrates so that said tube may be located in a substantially horizontal incubating position with said flat portion in contact with a supporting planar horizontal surface,
said neck having an inwardly protruding dam lying adjacent said chamber to prevent the flow of a liquid from the volume just above said flat portion into said neck when the Leighton tube is in its incubating position,
said neck communicating said chamber above said dam through a passage,
said cover slip having a culture segment, a handle, and a connecting segment,
said culture segment being flat and of a shape similar to and of dimensions not larger than said flat portion of said wall,
said handle lying substantially in a plane displaced from and parallel to that in which said culture segment lies and being connected to said culture segment by said connecting segment,
said handle and said connecting segment being of such dimensions that in its growth position said culture segment rests flat upon said flat portion inside said tube while said handle penetrates through said passage into and terminates within said 2. A Leighton tube assembly as described in claim 1 further characterized by
said tube being formed from a transparent material suitable for injection molding,
said tube being molded in two pieces, a first piece comprising said neck and said dam and a second piece comprising said chamber and said closed end, and first and second pieces being welded together.

3. A Leighton tube assembly as described in claim 1 further characterized by
said cover slip being formed from a transparent injection moldable material which is inert to most organic solvents.

4. A Leighton tube assembly as described in claim 1 further characterized by
means for engaging the cover slip to retain it in position within the tube.

5. A Leighton tube assembly as described in claim 1 further characterized by
means for guiding said culture segment into its growth position upon insertion of the cover slip into the tube.

6. A Leighton tube assembly as described in claim 5 further characterized by
means within the tube for engaging the cover slip to retain it in position within the tube.

7. A Leighton tube assembly as described in claim 6, further characterized by
said means for guiding and said means for engaging including at least one guide rib protruding from the inside surface of the tube.
said guide rib having a smooth surface angling from the tube wall opposite said flat portion and extending towards the closed end of the tube and towards said flat portion so that upon insertion of the cover slip into the tube the cover slip contacts the guide rib and the culture segment is guided into its growth position upon said flat portion, said guide rib terminating above said flat portion a distance just sufficient to allow the distal end of said culture segment to pass therebetween into said growth position, said guide rib preventing the displacement of said distal end vertically away from flat portion when said culture segment is in its growth position.

8. A Leighton tube assembly as described in claim 3 further characterized by said material out of which said cover slip is formed being cuttable, said culture segment being scored in at least one place to facilitate said cutting.

9. A Leighton tube assembly as described in claim 3 further characterized by said handle being serrated at its free end to facilitate secure grasping thereof by means of tweezers.

10. A Leighton tube assembly as described in claim 3 further characterized by said cover slip being treated to make it wettable so that cell growths will adhere thereto, said tube not being treated to make it wettable to that cell growths will not adhere thereto.

11. A Leighton tube as described in claim 1, further characterized by means for preventing the escape of said liquid from the chamber by capillary action between said cover slip and said dam.

12. A Leighton tube assembly as described in claim 1 further characterized by said connecting segment being formed at an angle with said culture segment which is steeper than the angle the dam makes with the flat portion so that when the cover slip is in position within the tube the connecting segment and the dam define a wedgeshaped gap between them with the wider portion of the wedge at the top.

13. A Leighton tube assembly as described in claim 12 further characterized by a spacer rib protruding within the tube from the chamber side of said dam, said spacer rib separating the connecting segment of the cover slip from the dam and extending sufficiently far from the dam so that capillary action cannot take place between the surfaces of the connecting segment and the dam.

14. A Leighton tube assembly as described in claim 7 further characterized by a spacer rib protruding within the tube from the chamber side of said dam, said spacer rib separating the connecting segment of the cover slip from the dam and extending sufficiently far from the dam so that capillary action cannot take place between the surfaces of the connecting segment and the dam.

15. A Leighton tube assembly comprising a tube closed at one end and open at the other, a neck adjacent said open end, a chamber toward said closed end which merges with said neck, means for closing said tube at said open end, and a cover slip, said chamber having a wall with a flat portion lying, at its outside, in a plane through which no part of said tube penetrates so that said tube may be located in a substantially horizontal incubating position with said flat portion in contact with supporting planar horizontal surface.

an inwardly protruding dam lying between said chamber and neck to prevent the flow of a liquid from the chamber into said neck when the Leighton tube is in its incubating position, said neck communicating with said chamber above said dam through a passage, said cover slip having a flat culture segment and a handle, said culture segment and said handle being disposed in separate planes, said handle extending through said passage into and terminating within said neck when the cover slip is positioned in said chamber.

* * * * *